United States Patent [19]

Rollmann

[11] 4,296,083

[45] Oct. 20, 1981

[54] ZEOLITE SYNTHESIS

[75] Inventor: Louis D. Rollmann, Princeton, N.J.

[73] Assignee: Mobil Oil Corporation, New York, N.Y.

[21] Appl. No.: 93,958

[22] Filed: Nov. 14, 1979

Related U.S. Application Data

[63] Continuation-in-part of Ser. No. 925,015, Jul. 17, 1978, abandoned, which is a continuation-in-part of Ser. No. 789,901, Apr. 22, 1977, abandoned.

[51] Int. Cl.$^3$ .............................................. C01B 33/28
[52] U.S. Cl. .................................. 423/329; 252/431 N; 252/455 Z; 260/326.61; 260/448 C; 423/330
[58] Field of Search ................................ 423/328–330, 423/118; 260/448 C, 326.61, 583 P; 252/431 N, 455 Z

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 3,832,449 | 8/1974 | Rosiwski et al. | 423/328 |
| 3,849,463 | 11/1974 | Dwyer et al. | 423/328 |
| 3,992,466 | 11/1976 | Plank et al. | 423/328 X |
| 4,025,571 | 5/1977 | Lago | 423/328 |
| 4,076,842 | 2/1978 | Plank et al. | 423/328 |

*Primary Examiner*—Edward J. Meros
*Attorney, Agent, or Firm*—C. A. Huggett; C. J. Speciale; G. W. Allen

[57] ABSTRACT

An improved method for synthesizing improved crystalline zeolites characterized by an alumina to silica mole ratio of not greater than 0.083 and a constraint index within the approximate range of 1 to 12 is provided. The improved method comprises forming a reaction mixture containing one or more sources of alkali metal oxide, organic nitrogen-containing cations, hydrogen ions, an oxide of silicon, water, and optionally, an oxide of aluminum, wherein the mole ratio for hydroxide ions/silica in said reaction mixture is zero and the mole ratio of H$^+$(additional)/silica in said reaction is between 0 and 1.0, and wherein the pH of said reaction mixture is at least about 7, and maintaining the reaction mixture at a temperature and pressure for a time necessary to crystallize therefrom said crystalline zeolite. Improvement in the present synthesis method resides, for example, in reduced crystallization time and reduced organic nitrogen-containing cation source requirement. Improvement in zeolite product from the present improved method resides, for example, in enhanced purity.

14 Claims, No Drawings

ZEOLITE SYNTHESIS

CROSS REFERENCE TO RELATED APPLICATIONS

This is a continuation-in-part of application Ser. No. 925,015, filed July 17, 1978, now abandoned, which is a continuation-in-part of application Ser. No. 789,901, filed Apr. 22, 1977, now abandoned.

BACKGROUND OF THE INVENTION

1. Field of the Invention

This invention relates to an improved method for synthesizing crystalline zeolites requiring a reaction mixture for crystallization thereof which contains an organic nitrogen-containing cation source. Zeolites which may be advantageously synthesized by the present improved method are characterized by an alumina to silica mole ratio of not greater than 0.083 and a constraint index within the approximate range of 1 to 12. The present improved method requires a zeolite reaction mixture composition comprising a mole ratio of hydroxide ion/silica of zero by conventional calculation procedures, a mole ratio of H+(additional)/silica of between 0 and 1.0, and a reaction mixture of pH of at least about 7.

This invention further relates to an improved crystalline zeolite product of the improved method of synthesis and to organic compound conversion in the presence of the improved zeolite as catalyst.

2. Description of the Prior Art

Zeolitic materials, both natural and synthetic, have been demonstrated in the past to have catalytic properties for various types of hydrocarbon conversions.

Certain zeolitic materials are ordered, porous crystalline zeolites having a definite crystalline structure within which there are a large number of smaller cavities which may be inter-connected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline zeolites. These zeolites can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as Ca/2, Sr/2, Na, K or Li is equal to unity. One type of cation may be exchanged either entirely or partially by another type of cation utilizing ion exchange techniques in a conventional manner. By means of such cation exchange, it has been possible to vary the properties of a given zeolite by suitable selection of the cation. The spaces between the tetrahedra are usually occupied by molecules of water prior to dehydration.

Prior art techniques have resulted in the formation of a great variety of synthetic zeolites. A number of these zeolites require the presence of a source of organic nitrogen-containing cations in the reaction mixture used to prepare them. Those zeolites include, for example, zeolite ZSM-5 (U.S. Pat. Nos. 3,702,886 and Re 29,948), zeolite ZSM-11 (U.S. Pat. No. 3,709,979), zeolite ZSM-12 (U.S. Pat. No. 3,832,449), zeolite ZSM-23 (U.S. Pat. No. 4,076,842), zeolite ZSM-35 (U.S. Pat. No. 4,016,245), zeolite ZSM-38 (U.S. Pat. No. 4,046,859), zeolite ZK-4 (U.S. Pat. No. 3,314,752), zeolite ZK-22 (U.S. Pat. No. 3,791,964), zeolite "alpha" (U.S. Pat. No. 3,375,205), zeolite "beta" (U.S. Pat. No. 3,308,069), a synthetic erionite (U.S. Pat. No. 3,699,139) and a synthetic offretite (U.S. Pat. No. 3,578,398). A method for synthesizing ZSM-5, ZSM-12, ZSM-35 and ZSM-38 is disclosed in U.S. Pat. No. 4,151,189.

Applicant knows of no prior art methods of crystalline zeolite synthesis, said synthesis requiring a source of organic nitrogen-containing cations in the reaction mixture used therein, utilizing the present improvement.

SUMMARY OF THE INVENTION

An improved method for preparing an improved crystalline zeolite exhibiting enhanced purity as synthesized is provided which comprises forming a reaction mixture containing one or more sources of an alkali metal oxide, any organic nitrogen-containing compounds required for preparation of the particular zeolite to be synthesized, hydrogen ions, an oxide of silicon, water, and, optionally, an oxide of aluminum, wherein the mole ratio of hydroxide ions/silica in said reaction mixture is zero and the mole ratio of H+(additional)/silica in said reaction mixture is between 0 and 1.0, and wherein the pH of said reaction mixture is at least about 7, preferably from about 7 to about 12, and maintaining the reaction mixture at a temperature and pressure for a time necessary to crystallize therefrom said crystalline zeolite. Said crystalline zeolite is characterized by an alumina to silica mole ratio of not greater than 0.083 and a constraint index within the approximate range of 1 to 12. Crystalline zeolites thus characterized include ZSM-5, ZSM-11, ZSM-12, ZSM-23, ZSM-35, ZSM-38, and other similar materials.

Reaction conditions include heating the reaction mixture to a temperature of from about 70° C. to about 300° C. for a period of time of from about 1 hour to about 180 days. At a given reaction temperature, crystallization time can be significantly reduced from that required by the prior art by the present improved method. New zeolite structures may result as well by the present method. Further, the amount of organic nitrogen-containing cation source required in the reaction mixture can be reduced from that required by the prior art by the present improved method. Still further, the crystalline zeolite synthesized by the present improved method can be of higher purity than normally obtainable by prior art methods of synthesis.

DESCRIPTION OF SPECIFIC EMBODIMENTS

The present invention offers a means of synthesizing improved crystalline zeolites requiring a reaction mixture for crystallization thereof which contains a source of organic nitrogen-containing cations.

The crystalline zeolites synthesized herein are members of a novel class of zeolitic materials which exhibit unusual properties. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The alumina to silica mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with an alumina to silica ratio of not greater than 0.083 are useful, it is preferred in some applications to use zeolites having lower alumina to silica mole ratios of at most about 0.033. In addition, zeolites as otherwise characterized herein but which are substantially free of aluminum, i.e., having alumina to silica mole ratios of 0.000625 and even much lower, are found to be useful and even preferable in some instances. Such "high silica" or "highly siliceous" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally low alumina to silica mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (C.I.) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g. 14 or 15 with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, and other similar materials.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these are incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. Zeolite ZSM-38 and the conventional preparation thereof are described in U.S. Pat. No. 4,046,859, the disclosure of which is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of alumina to silica is essentially unbounded. The incorporation of the identified patents should therefore not be construed as limiting the disclosed crystalline zeolites to those having the specific alumina-silica mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. The may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

In a preferred aspect of this invention, the zeolites hereof are selected as those providing among other things a crystal framework density, the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, an alumina to silica mole ratio of not greater than 0.003 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the focus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

In the present improved method of zeolites synthesis, a reaction mixture is formed containing one or more sources of alkali metal oxide, organic nitrogen-containing cations, hydrogen ions, an oxide of silicon, water and, optionally, an oxide of aluminum. The composition of the reaction mixture must have a hydroxide ion/silica mole ratio of zero, as calculated by conventional procedures. The composition must also have an H+(additional)/silica mole ratio of between zero and 1.0. The reaction mixture, further, must have a pH of at least 7, preferably from between about 7 and 12.

The sources of alkali metal oxide may be, for example, sodium, lithium or potassium hydroxides, oxides, carbonates, halides (e.g. chlorides and bromides), sulfates, nitrates, acetates, silicates, aluminates, phosphates and salts of carboxylic acids.

The sources of organic nitrogen-containing cations, depending, of course, on the particular zeolite product to result from crystallization from the reaction mixture, may be primary, secondary or tertiary amines or quaternary ammonium compounds. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium and chlorine. Non-limiting examples of amines useful herein include the compounds of trimethylamine, triethylamine, tripropylamine, ethylenediamine, propanediamine, butanediamine, pentanediamine, hexanediamine, methylamine, ethylamine, propylamine, butylamine, diamethylamine, diethylamine, dipropylamine, benzylamine, aniline, pyridine, piperidine and pyrrolidine. Amines useful herein are those having a $pK_a$ in the range of between about 7 and about 12.

The sources of hydrogen ions may be, for example, HCl, $H_2SO_4$, $H_3PO_4$, $HNO_3$, carboxylic acids, aluminum sulfates, nitrates, chlorides, phosphates or acid salts of primary, secondary or tertiary amines. Hydrogen ions are generated from the aforenoted aluminum salts by hydrolysis. Taking, for example, aluminum sulfate as illustrative, hydrolysis of this compound, a salt of a weak base and a strong acid would yield:

$$Al_2(SO_4)_3 + 6H_2O \rightarrow 2Al(OH)_3 + 6H^+ + 3SO_4^{-2}$$

Sources of silicon oxides may be, for example, silica sols, alkali metal silicates, silica gels, silicic acid or aluminosilicates.

Sources of aluminum oxides may be, for example, alkali metal aluminates, aluminum metal, hydrated aluminum oxides or aluminum salts of acids such as $H_2SO_4$, HCl, $HNO_3$ and the like. If no source of aluminum is employed in the reaction mixture, the resulting zeolite will probably be a highly siliceous zeolite.

In general, the reaction mixture for the present improved synthesis process will have a composition, in terms of mole ratios of oxides, as follows:

|  | Broadly Acceptable | Preferred | Most Preferred |
|---|---|---|---|
| $Al_2O_3/SiO_2$ | 0–0.083 | 0.005–0.06 | 0.01–0.05 |
| $OH^-/SiO_2$ | 0 | 0 | 0 |
| $H_2O/SiO_2$ | 5–200 | 10–100 | 10–100 |
| $M/SiO_2$ | 0.01–5.0 | 0.1–2.0 | 0.2–1.0 |
| $R/SiO_2$ | 0.01–3.0 | 0.04–2.0 | 0.1–1.0 |
| $H^+(additional)/SiO_2$ | 0–1.0 | 0–0.6 | 0–0.4 | wherein R is an organic nitrogen-containing cation or organic nitrogen-containing cation source and M is an alkali metal ion.

Specifically, when ZSM-5 is the desired zeolite product of the present improved synthesis process, the reaction mixture will have a composition, in terms of mole ratios of oxides, as follows:

$Al_2O_3/SiO_2 = 0$–$0.083$
$OH^-/SiO_2 = 0$
$H_2O/SiO_2 = 5$–$200$
$M/SiO_2 = 0.01$–$3.0$
$R/SiO_2 = 0.01$–$1.0$
$H^+(additional)/SiO_2 = 0$–$1.0$ wherein R is a tetrapropylammonium cation or an alkylamine or diamine and M is an alkali metal ion. The reaction mixture must be maintained at a temperature of from about 100° F. to about 400° F. for a period of time of from about 3 hours to about 150 days until crystals form. Thereafter, the crystals are separated from the reaction medium and recovered. Separation may be accomplished by, for example, cooling the whole to room temperature, filtering and water washing.

When ZSM-11 is the desired zeolite product of the present improved synthesis process, the reaction mixtures will have a composition, in terms of mole ratios of oxides, as follows:

$Al_2O_3/SiO_2 = 0$–$0.083$
$OH^-/SiO_2 = 0$
$H_2O/SiO_2 = 5$–$100$
$M/SiO_2 = 0.1$–$2.0$
$R/SiO_2 = 0.04$–$1.0$
$H^+(additional)/SiO_2 = 0$–$1.0$ wherein R is a tetrabutylammonium cation or alkylamine, or diamine and M is an alkali metal ion. The reaction mixture must be maintained at a temperature of from about 100° F. to about 400° F. for a period of time from about 4 hours to about 180 days until crystals form. Thereafter, the crystals are separated from the reaction medium and recovered. Separation may be accomplished by, for example, cooling the whole to room temperature, filtering and water washing.

When ZSM-12 is the desired zeolite product of the present improved synthesis process, the reaction mixture will have a composition, in terms of mole ratios of oxides, as follows:

$Al_2O_3/SiO_2 = 0$–$0.025$

OH$^-$/SiO$_2$=0
H$_2$OSiO$_2$=5-100
M/SiO$_2$=0.1-3.0
R/SiO$_2$=0.1-2.0
H$^+$(additional)/SiO$_2$=0-1.0 wherein R is a tetraethylammonium cation or a cation derived from triethylamine and M is an alkali metal ion. The quantity of hydroxide ions is calculated from only the inorganic sources of alkali without any organic base contribution. The reaction mixture must be maintained at a temperature of from about 100° F. to about 400° F. for a period of time of from about 6 hours to about 180 days until crystals form. Thereafter, the crystals are separated from the reaction medium and recovered. Separation may be accomplished by, for example, cooling the whole to room temperature, filtering the water washing.

When ZSM-23 is the desired zeolite product of the present improved synthesis process, the reaction mixture will have a composition, in terms of mole ratios of oxides, as follows:

Al$_2$O$_3$/SiO$_2$=0-0.083
OH$^-$/SiO$_2$=0
H$_2$O/SiO$_2$=5-100
M/SiO$_2$=0.1-2.0
R/SiO$_2$=0.1-1.0
H$^-$(additional)/SiO$_2$=0-1.0 wherein R is a cation derived from pyrrolidine and M is an alkali metal ion. The quantity of hydroxide ions is calculated only from the inorganic sources of alkali without any organic base contribution. The reaction mixture must be maintained at a temperature of from about 100° F. to about 400° F. for a period of time of from about 6 hours to about 180 days until crystals form. Thereafter, the crystals are separated from the reaction medium and recovered. Separation may be accomplished by, for example, cooling the whole to room temperature, filtering and water washing.

When ZSM-35 is the desired zeolite product of the present improved synthesis process, the reaction mixture will have a composition, in terms of mole ratios of oxides, as follows:

Al$_2$O$_3$/SiO$_2$=0-0.083
OH$^-$/SiO$_2$=0
H$_2$O/SiO$_2$=5-100
M/SiO$_2$=0.1-3.0
R/SiO$_2$=0.05-2.0
H$^+$(additional)/SiO$_2$=0-1.0 wherein R is a cation derived from ethylenediamine, propanediamine, butenediamine, or pyrrolidine and M is an alkali metal ion. The quantity of hydroxide ions is calculated from only the inorganic sources of alkali without any organic base contribution. The reaction mixture must be maintained at a temperature of from about 100° F. to about 400° F. for a period of time of from about 6 hours to about 180 days until crystals form. Thereafter, the crystals are separated from the reaction medium and recovered. Separation may be accomplished by, for example, cooling the whole to room temperature, filtering and water washing.

When ZSM-38 is the desired zeolite product of the present improved synthesis process, the reaction mixture will have a composition, in terms of mole ratios of oxides, as follows:

Al$_2$O$_3$/SiO$_2$=0-0.083
OH$^-$/SiO$_2$=0
H$_2$O/SiO$_2$=5-100
M/SiO$_2$=0.1-3.0
R/SiO$_2$=0.1-2.0
H$^+$(additional)/SiO$_2$=0-1.0 wherein R is derived from a 2-(hydroxyalkyl) trialkylammonium compound wherein alkyl is a methyl, ethyl or a combination thereof, and M is an alkali metal ion. The reaction mixture must be maintained at a temperature of from about 100° F. to about 400° F. for a period of time of from about 6 hours to about 180 days until crystals form. Thereafter, the crystals are separated from the reaction medium and recovered. Separation may be accomplished by, for example, cooling the whole to room temperature, filtering and water washing.

It is recalled that in calculating the mole ratio of hydroxide ions/silica, it is conventional to calculate hydroxide by summing moles of OH$^-$, whether added as NaOH, as quaternary ammonium hydroxide, as sodium silicate (NaOH+SiO$_2$), as sodium aluminate (NaOH+Al$_2$O$_3$), or the like, and to subtract therefrom the sum any moles of acid added. Acid may be added simply as HCl, HNO$_3$, H$_2$SO$_4$, acetic acid, and the like or it may be added as an aluminum sulfate (Al$_2$O$_3$+H$_2$SO$_4$), chloride (Al$_2$O$_3$+HCl), nitrate (Al$_2$O$_3$+HNO$_3$), etc. In particular, no contribution is assigned to organic bases such as amines in this calculation.

Although the usefulness of this invention is to be found with quaternary ammonium cations at OH$^-$/SiO$_2$ ratios below those recognized earlier, it is with the amines that this invention is ideally suited. Amines present in reaction mixtures having an OH$^-$/SiO$_2$ ratio of 0.01 are protonated when further acid is added. Until said additional acid exceeds the amine present, the pH remains above 7.

In a conventional calculation which does not consider amines, the total moles of acid could thereby exceed the moles of hydroxide added in said reaction mixture and subtraction would thereby lead to apparent "negative" OH$^-$/SiO$_2$ ratios. A negative ratio is, of course, not possible since the true moles of hydroxide (per liter) in an aqueous mixture are always positive and equal to $10^{-14}$ divided by the moles per liter of acid. Maintaining the convention which has been established in describing reaction mixture compositions, we define the quantity of acid added in excess of the hydroxide added by the ratio H$^+$(additional)/SiO$_2$ and, recognizing the impossibility of negative OH$^-$/SiO$_2$ ratios, the OH$^-$/SiO$_2$ ratio was arbitrarily assigned to a value of zero. The casual experimenter must be cautioned that, as will be well known to those skilled in the art of zeolite crystallization, not all possible combinations within a broadly defined composition range will be equally effective. Some combinations will indeed be unsuccessful or impractical.

The improved zeolites prepared by the present improved method may be used for organic compound conversion in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Chart of the Elements especially rare earth metals. However, in the case of Group IA metals, the cation content should in no case be so large as to effectively inactivate the catalyst.

As in the case of many catalysts, it is desirable to incorporate the improved catalyst prepared by the present improved method with another material resistant to the temperature and other conditions employed in some organic compound conversion processes. Such matrix materials include active and inactive materials and synthetic or naturally occurring zeolites as well as inorganic material such as clays, silica and/or metal oxides. The latter may be either naturally occurring or in the form of gelatinous precipitates, sols or gels including mixtures of silica and metal oxides. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It may be desirable to provide a catalyst having good crush strength so it may be used in a process where the catalyst is subjected to rough handling, such as in a fluidized system, which may tend to break the catalyst down into powder-like materials which cause problems in processing.

Naturally occurring clays which can be composited with the improved zeolites prepared hereby include the montmorillonite and kaolin families, which include the sub-bentonites and the kaolins commonly known as Dixie, McNammee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites made hereby can be composited with one or more porous matrix materials such as alumina, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel. A mixture of these components, one with the other and/or with a clay, could also be used. The relative proportions of zeolite and inorganic oxide gel matrix and/or clay vary widely with the crystalline aluminosilicate content ranging from about 1 to about 90 percent by weight and more usually in the range of about 2 to about 50 percent by weight of the composite.

Zeolites prepared by the present improved method are valuable catalysts or catalyst components in various organic compound conversion processes, e.g. hydrocarbon compound and oxygenate, such as methanol, conversion processes. Such processes include, for example, alkylation of aromatics with olefins; aromatization of normally gaseous olefins and paraffins; aromatization of normally liquid low molecular weight parrafins and olefins; isomerization of aromatics, paraffins and olefins; disproportionation of aromatics; transalkylation of aromatics; oligomerization of olefins; cracking and hydrocracking. All of the foregoing catalytic processes are of value since they result in upgrading of the organic charge being processed.

The process for upgrading reformates wherein a zeolite prepared in accordance herewith is employed as catalyst generally involves contact during processing with a reformate or reformer effluent, with or without added hydrogen, at a temperature between 500° F. and about 1100° F. and preferably between about 550° F. and about 1000° F. The reaction pressure in such operation is generally within the range of about 25 and about 2000 psig and preferably about 50 to about 1000 psig. The liquid hourly space velocity, i.e. the liquid volume of hydrocarbon per hour per volume of catalyst, is between about 0.1 and about 250, and preferably between about 1 and 100. Although hydrogen is not essential to this process, when it is used the molar ratio of hydrogen to hydrocarbon charge employed is between about 0.1 and about 80 and preferably between about 1 and about 10.

Oligomerization of olefins, i.e. olefins having 2 to 10 carbon atoms, is effectively carried out with the zeolite prepared in accordance herewith as catalyst. Such reaction is suitably effected at a temperature between about 550° F. and about 1150° F., a pressure between about 0.01 and about 1000 psig and a weight hourly space velocity within the approximate range of 0.1 to 1000.

Alkylation of aromatic hydrocarbons, e.g. benzene, with an alkylating agent such as an alkyl halide, an alcohol or an olefin, is also readily effected in the presence of the presently made zeolite as catalyst with reduced aging. Alkylation conditions include a temperature between about 400° F. and about 1000° F., a pressure between about 25 and about 1000 psig, an aromatic hydrocarbon/alkylating agent mole ratio of 2 to 200 and an alkylating agent weight hourly space velocity within the approximate range of 0.5 to 50.

Xylene isomerization is another reaction suitably conducted in the presence of the zeolite made in accordance herewith as catalyst. Isomerization conditions include a temperature between about 300° F. and about 900° F., a pressure between about 25 and about 1000 psig and a weight hourly space velocity within the approximate range of 0.2 to 100.

Aromatics, such as, for example, toluene, may be disproportionated in the presence of the presently made zeolite under a temperature of from about 450° F. to about 1100° F., a pressure of from about 50 psig to about 800 psig and a liquid hourly space velocity within the approximate range of about 0.1 to about 20. Aliphatic hydrocarbons may also be disproportionated in the presence of zeolite prepared by the present improved method at a temperature of from about 350° F. to about 900° F., a pressure between 0 and 3,000 psig and a liquid hourly space velocity of between about 0.01 and about 5.

When the conversion of organic compounds with the presently made zeolite as catalyst is cracking, catalytic conversion conditions should be maintained within certain ranges, including a temperature of from about 700° F. to about 1200° F., preferably from about 800° F. to about 1000° F., a pressure of from about atmospheric to about 200 psig, and a liquid hourly space velocity of from about 0.5 $hr^{-1}$ to about 50 $hr^{-1}$, preferably from about 1 $hr^{-1}$ to about 10 $hr^{-1}$. When the conversion is hydrocracking, catalytic conversion conditions should be maintained within somewhat different ranges, including a temperature of from about 400° F. to about 1000° F., preferably from about 500° F. to about 850° F., a pressure of from about 500 psig to about 3500 psig, a liquid hourly space velocity of from about 0.1 $hr^{-1}$ to about 10 $hr^{-1}$, preferably from about 0.2 $hr^{-1}$ to about 5 $hr^{-1}$, and a hydrogen/hydrocarbon ratio of from about 1000 scf/bbl to about 20,000 scf/bbl, preferably from about 3,000 scf/bbl to about 10,000 scf/bbl.

It may be desirable in some instances to add a hydrogenation/dehydrogenation component to the zeolite prepared in accordance herewith for use as catalyst. The amount of the hydrogenation/dehydrogenation component employed is not narrowly critical and can range from about 0.01 to about 30 weight percent based on the entire catalyst. A variety of hydrogenation components may be combined with either the zeolite and/or matrix in any feasible manner which affords intimate contact of the components, employing well known techniques such as base cogellation, mechanical admixture of one component with the other and the like. The hydrogenation component can include metals, oxides and sulfides of metals of the Periodic Chart of the Elements (Fisher Scientific Company, Cat. No. 5-702-10, 1978) which fall in Group VIA including chromium, molybdenum, tungsten and the like; Group IIB including zinc and cadmium; Group VIII including cobalt, nickel, platinum, palladium, ruthenium, rhodium, osmium and iridium; Group IVB such as germanium and tin and combinations of metals, sulfides and oxides of metals of Group VIA and VIII, such as nickel-tungsten-sulfide, cobalt oxide-molybdenum oxide and the like. Pre-treatment before use varies depending on the hydrogenation component present. For example, with components such as nickel-tungsten, cobalt-molybdenum, platinum and palladium, the catalyst may desirably be sulfided. With metals like platinum or palladium, a hydrogenation step may also be employed. These techniques are well known in the art and are accomplished in a conventional manner.

In order to more fully illustrate the nature of the invention and the manner of practicing same, the following examples are presented.

EXAMPLE 1

In accordance with the prior art method of preparing zeolite ZSM-5, to a solution of 63.3 grams Q-brand sodium silica (28.5 wt. % $SiO_2$, 7.75 wt. % $Na_2O$ and 63.75 wt. % $H_2O$) in 79.2 grams of water in a polypropylene bottle was added a solution of 2.05 grams $Al_2(SO_4)_3.16H_2O$, 3.8 grams $H_2SO_4$ and 7.85 grams tetrapropylammonium bromide in 108.3 grams of water. After vigorous mixing the pH of the mixture was measured to be $\geq 10$.

The bottle was placed in a steam chest at 90°-95° C. The reaction mixture had a molar composition as follows:

$Al_2O_3/SiO_2 = 0.011$
$OH^-/SiO_2 = 0.20$
$H_2O/SiO_2 = 42$
$M/SiO_2 = 0.53$
$R/SiO_2 = 0.10$
$H^+(\text{additional})/SiO_2 = 0$ After 30 days, a sample of the gel was taken, washed with water and dried. An X-ray diffraction pattern showed the sample to contain about 40% ZSM-5 together with amorphous material.

EXAMPLE 2

In accordance with the present improved method of preparing zeolite ZSM-5, to a solution of 63.3 grams Q-brand sodium silicate in 79.2 grams of water in a polypropylene bottle was added a solution of 2.05 grams $Al_2(SO_4)_3.16H_2O$, 7.2 grams $H_2SO_4$ and 7.85 grams tetrapropylammonium bromide in 108.3 grams of water. The hydrogen (acid) ions in this reaction mixture were present in amount equivalent to the $OH^-$ added. After vigorous mixing the pH was determined to be 7. The bottle was then placed in a steam chest at 90°-95° C. The reaction mixture had a molar composition as follows:

$Al_2O_3/SiO_2 = 0.011$
$OH^-/SiO_2 = 0$
$H_2O/SiO_2 = 42$
$M/SiO_2 = 0.53$
$R/SiO_2 = 0.10$
$H^{30}$ (additional)$/SiO_2 = 0$ Although successful crystallization was noted earlier, the product ZSM-5 was removed, washed, and dried after 30 days in the steam chest. The X-ray diffraction pattern showed 100% ZSM-5. Scanning electron micrograms showed the material to be relatively uniform crystals of 6–12 micron diameter.

EXAMPLES 3–6

In these examples, prior art and present improved methods of syntheses of zeolite ZSM-35 were conducted. Crystallization at 100° C. was conducted in polypropylene bottles under static conditions in a steam chest. The silicate source was Q-brand (27.8% $SiO_2$, 8.42% $Na_2O$) and the alumina source was $Al_2(SO_4)_2.16H_2O$. The organic nitrogen-containing cation source was pyrrolidine. Reaction mixture compositions (mole ratios), total days in the steam chest for crystallization to occur and zeolite product compositions are tabulated in Table IV, hereinafter presented. It is observed from these examples that prior art methods (Examples 5 and 6) fail to compare favorably with the present improved method of synthesis (Examples 3 and 4) for zeolite ZSM-35. After only 35 and 39 days in the steam chest, 100% ZSM-35 was obtained from the improved method of Examples 3 and 4. After as many as 85 days in the steam chest for the reaction mixture of Example 5, the product contained 50% ZSM-35 and 50% mordenite. After 70 days in the steam chest for the reaction mixture of Example 6, only 10% ZSM-35 resulted.

TABLE IV

| Example | Reaction Mixture Composition | | | | | | |
|---|---|---|---|---|---|---|---|
| | $Al_2O_3/SiO_2$ | $H_2O/SiO_2$ | $OH^-/SiO_2$ | $Na/SiO_2$ | $H^+$(additional)$/SiO_2$ | $R/SiO_2$ | pH |
| 3 | 0.033 | 39 | 0 | 0.59 | 0.15 | 0.68 | 11–12 |
| 4 | 0.033 | 39 | 0 | 0.59 | 0.02 | 0.27 | 11–12 |
| 5 | 0.033 | 40 | 0.29 | 0.59 | 0 | 0.30 | 13–14 |
| 6 | 0.033 | 39 | 0.29 | 0.59 | 0 | 0.19 | 13–14 |

| Example | Days | Zeolite | Product Composition | | | | |
|---|---|---|---|---|---|---|---|
| | | | $Al_2O_3/SiO_2$ | Al/uc* | Na/uc* | N/uc* | C/N |
| 3 | 35 | 100% ZSM-35 | 0.034 | 2.3 | 0.1 | 4.1 | 4.5 |
| 4 | 39 | 100% ZSM-35 | 0.037 | 2.5 | 0.2 | 3.9 | 4.5 |
| 5 | 85 | 50% ZSM-35 + 50% Mordenite | — | — | — | — | — |
| 6 | 70 | 10% ZSM-35 | — | — | — | — | — |

*uc = Unit cell, assumed to contain 36 Si and Al tetrahedra.

EXAMPLES 7–10

In these examples, the present improved methods of synthesis of zeolite ZSM-35 were conducted. Crystallization at 100° C. was conducted in polypropylene bottles under static conditions in a steam chest. The silicate source was Q-brand (27.8% $SiO_2$, 8.42% $Na_2O$) and the alumina source was $Al_2(SO_4)_3.16H_2O$. The organic nitrogen-containing source was 1, 4-butanediamine. Reaction mixture compositions (mole ratios), total days in the steam chest for crystallization to occur and zeolite product compositions are tabulated in Table V, hereinafter presented.

and zeolite product conditions are given below in Table VII:

TABLE VII

|  | Example 14 | Example 15 |
| --- | --- | --- |
| Reaction Mixture Composition |  |  |
| $Al_2O_3/SiO_2$ | 0.033 | 0.033 |
| $OH^-/SiO_2$ | 0 | 0 |
| $H_2O/SiO_2$ | 39 | 39 |
| $Na/SiO_2$ | 0.59 | 0.59 |
| $R/SiO_2$ | 0.33 | 0.14 |
| $H^+$(additional)/$SiO_2$ | 0.14 | 0.03 |
| Days in Steam Chest | 3 | 3 |
| Product Composition | 98% ZSM-35 | 95% ZSM-35 |

TABLE V

| Example | $Al_2O_3/SiO_2$ | $H_2O/SiO_2$ | $OH^-/SiO_2$ | $Na/SiO_2$ | $H^+$(add'l.)/$SiO_2$ | $R/SiO_2$ | Days | Product Composition |
| --- | --- | --- | --- | --- | --- | --- | --- | --- |
| 7 | 0.033 | 39 | 0 | 0.59 | 0.43 | 0.34 | 210 | 85% ZSM-35 |
| 8 | 0.033 | 39 | 0 | 0.59 | 0.15 | 0.34 | 37 | 100% ZSM-35 |
| 9 | 0.033 | 39 | 0 | 0.59 | 0.02 | 0.14 | 32 | 100% ZSM-35 |
| 10 | 0.033 | 39 | 0 | 0.59 | 0.02 | 0.14 | 39 | 100% ZSM-35 |

EXAMPLE 11

In this example, the same procedure, conditions and reactants as Examples 7–10 were employed, with the exception that the crystallization was conducted with stirring, rather than static conditions. The reaction mixture had the following composition:

$Al_2O_3/SiO_2=0.033$
$OH^-/SiO_2=0$
$H_2O/SiO_2=39$
$Na/SiO_2=0.59$
$R/SiO_2=0.14$
$H^+$(additional)$SiO_2=0.02$ After 17 days in the steam chest, the product was improved, washed and dried. An x-ray diffraction pattern showed the product to contain 100% ZSM-35.

EXAMPLES 12–13

In these examples, the same procedure, conditions and reactants as Examples 7–10 were employed, except that the organic nitrogen-containing source utilized was 1, 3-propanediamine. The reaction mixture compositions (mole ratios), total days in the steam chest for crystallization to occur and zeolite product compositions are as given below in Table VI.

TABLE VI

|  | Example 12 | Example 13 |
| --- | --- | --- |
| Reaction Mixture Composition |  |  |
| $Al_2O_3/SiO_2$ | 0.033 | 0.033 |
| $OH^-/SiO_2$ | 0 | 0 |
| $H_2O/SiO_2$ | 39 | 39 |
| $Na/SiO_2$ | 0.59 | 0.59 |
| $R/SiO_2$ | 0.68 | 0.27 |
| $H^+$(additional)/$SiO_2$ | 0.15 | 0.02 |
| Days in Steam Chest | 35 | 39 |
| Product Composition | 100% ZSM-35 | 100% ZSM-35 |

EXAMPLES 14–15

In these examples, the same procedure, conditions and reactants as Examples 7–10 were utilized, except that the crystallization temperature was 160° C. and teflon bottles were used, rather than polypropylene bottles. The reaction mixture composition (mole ratios), total days in the steam chest for crystallization to occur

EXAMPLE 16

In accordance with the present improved method of preparing zeolite ZSM-5, crystallization at 100° C. was conducted in a polypropylene bottle with stirring in a steam chest. The silicate source was Q-brand (27.8% $SiO_2$, 8.42% $Na_2O$) and the alumina source was $Al_2(SO_4)_3.16H_2O$. The organic nitrogen-containing cation source was ethylenediamine. The reaction mixture had a molar composition as follows:

$Al_2O_3/SiO_2=0.033$
$OH^-/SiO_2=0$
$H_2O/SiO_2=39$
$Na/SiO_2=0.59$
$R/SiO_2=0.14$
$H^+$(additional)/$SiO_2=0.02$ The product was removed, washed and dried after 31 days in the steam chest. An x-ray diffraction pattern of the product showed 75% ZSM-5.

EXAMPLE 17

In this example, the same procedures, conditions and reactants as Example 16 were utilized, except for the organic nitrogen-containing source was 1, 6-hexane diamine rather than ethylenediamine. Also the crystallization was conducted under static conditions, i.e. without stirring. The reaction mixture had the following composition:

$Al_2O_3/SiO_2=0.011$
$OH^-/SiO_2=0$
$H_2O/SiO_2=44$
$Na/SiO_2=0.59$
$R/SiO_2=0.29$
$H^+$(add'l.)/$SiO_2=0.19$ After 154 days in the steam chest, the product was analyzed as 100% ZSM-5.

EXAMPLE 18

In accordance with the present improved method of preparing zeolite ZSM-5, crystallization at 200° C. was conducted in a teflon bottle under static conditions in a steam chest. The silicate source was Q-brand (27.8% $SiO_2$, 8.42% $Na_2O$) and the alumina source was $Al_2(SO_4)_3.16H_2O$. The organic nitrogen-containing cation source was ethylenediamine. The reaction mixture had a molar composition as follows:

$Al_2O_3/SiO_2 = 0.033$
$OH^-/SiO_2 = 0$
$H_2O/SiO_2 = 39$
$Na/SiO_2 = 0.59$
$R/SiO_2 = 0.14$
$H^+(add'l.)/SiO_2 = 0.03$ The product was removed, washed and dried after 7 days in the steam chest. An x-ray diffraction pattern of the product showed 50% ZSM-5 and 30% mordenite.

EXAMPLE 19

A sample of crystalline aluminosilicate zeolite ZSM-5 prepared as in Example 2 was evaluated for catalytic activity with a five-component feedstock of n-hexane, 3-methylpentane, 2, 3-dimethylbutane, benzene and toluene at 200 psig, a weight hourly space velocity (WHSV) of 2.9 $hr^{-1}$, a temperature of 427° C. and a hydrogen/hydrocarbon mole ratio of 3.6. This zeolite, after exchange, provided 94% conversion of n-hexane and 46% conversion of 3-methylpentane. Of the converted paraffin charge, 11% reacted with benzene and toluene to produce alkyl aromatics.

EXAMPLE 20

A sample of ZSM-35 was prepared as in Example 3, but a temperature of 160° C. and with $R/SiO_2 = 0.14$ and $H^+(additional)/SiO_2 = 0.03$. The ZSM-35 product was evaluated for catalytic activity with a feedstock as in Example 7. Test conditions were 200 psig, 3.2 $hr^{-1}$ WHSV, 427° C. and a hydrogen/hydrocarbon mole ratio of 4.8. This ZSM-35 converted 96% n-hexane and 20% 3-methylpentane.

What is claimed is:

1. A method for synthesizing zeolites, said zeolites characterized by an alumina to silica mole ratio of not greater than 0.083 and a constraint index within the approximate range of 1 to 12, which comprises forming a reaction mixture containing one or more sources of alkali metal oxide, organic nitrogen-containing cations provided by an amine, hydrogen ions, an oxide of silicon, water and, optionally, an oxide of aluminum, in which the composition, in terms of mole ratios of oxides, is as follows:

$Al_2O_3/SiO_2 = 0-0.083$
$OH^-/SiO_2 = 0$
$H_2O/SiO_2 = 5-200$
$M/SiO_2 = 0.01-5.0$
$R/SiO_2 = 0.01-3.0$
$H^+(additional)/SiO_2 = 0-1.0$ wherein R is an organic nitrogen-containing cation source, M is an alkali metal ion, and wherein the pH of said reaction mixture is at least about 7 and maintaining the reaction mixture at a temperature and pressure for a time necessary to crystallize therefrom said zeolite.

2. The method of claim 1 wherein said zeolites are selected from the group consisting of ZSM-5, ZSM-11, ZSM-12, ZSM-23, ZSM-35 and ZSM-38.

3. The method of claim 1 wherein said organic nitrogen-containing cation source is an amine having a $pK_a$ in the range of between about 7 and about 12.

4. The method of claim 3 wherein said amine is selected from the group consisting of primary amines, secondary amines and tertiary amines.

5. The method of claim 3 wherein said amine is selected from the group consisting of triethylamine, trimethylamine, tripropylamine, ethylenediamine, propanediamine, butanediamine, pentanediamine, hexanediamine, methylamine, ethylamine, propylamine, butylamine, dimethylamine, diethylamine, dipropylamine, benzylamine, aniline, pyridine, piperidine and pyrrolidine.

6. The method of claim 1 wherein the composition in terms of mole ratios of oxides is as follows:

$Al_2O_3/SiO_2 = 0.005-0.06$
$OH^-/SiO_2 = 0$
$H_2O/SiO_2 = 10-100$
$M/SiO_2 = 0.1-2.0$
$R/SiO_2 = 0.04-2.0$
$H^+(additional)/SiO_2 = 0-0.6$ 7. The method of claim 1 wherein the composition in terms of mole ratios of oxides is as follows:

$Al_2O_3/SiO_2 = 0.01-0.05$
$OH^-/SiO_2 = 0$
$H_2O/SiO_2 = 10-100$
$M/SiO_2 = 0.2-1.0$
$R/SiO_2 = 0.1-1.0$
$H^+(additional)/SiO_2 = 0-0.4$ 8. The method of claim 1 wherein said pH is between about 7 and about 12.

9. The method of claim 8 wherein said pH is 7.

10. The method of claim 1 wherein the zeolite prepared is ZSM-5 and said reaction mixture has a composition in terms of mole ratios of oxides as follows:

$Al_2O_3/SiO_2 = 0-0.083$
$OH^-/SiO_2 = 0$
$H_2O/SiO_2 = 5-200$
$M/SiO_2 = 0.01-3.0$
$R/SiO_2 = 0.01-1.0$
$H^+(additional)/SiO_2 = 0-1.0$ wherein R is an alkylamine or diamine and M is an alkali metal ion.

11. The method of claim 1 wherein the zeolite prepared is ZSM-11 and said reaction mixture has a composition in terms of mole ratios of oxides as follows:

$Al_2O_3/SiO_2 = 0-0.083$
$OH^-/SiO_2 = 0$
$H_2O/SiO_2 = 5-100$
$M/SiO_2 = 0.1-2.0$
$R/SiO_2 = 0.04-1.0$
$H^+(additional)/SiO_2 = 0-1.0$ wherein R is alkylamine or diamine and M is an alkali metal ion.

12. The method of claim 1 wherein the zeolite prepared is ZSM-12 and said reaction mixture has a composition in terms of mole ratios of oxides as follows:

$Al_2O_3/SiO_2 = 0-0.025$
$OH^-/SiO_2 = 0$
$H_2O/SiO_2 = 5-100$
$M/SiO_2 = 0.1-3.0$
$R/SiO_2 = 0.1-2.0$
$H^+(additional)/SiO_2 = 0-1.0$ wherein R is a cation derived from triethylamine and M is an alkali metal ion.

13. The method of claim 1 wherein the zeolite prepared is ZSM-23 and said reaction mixture has a composition in terms of mole ratios of oxides as follows:

$Al_2O_3/SiO_2 = 0-0.083$
$OH^-/SiO_2 = 0$
$H_2O/SiO_2 = 5-100$
$M/SiO_2 = 0.1-2.0$
$R/SiO_2 = 0.1-1.0$
$H^+(additional)/SiO_2 = 0-1.0$ wherein R is a cation derived from pyrrolidine and M is an alkali metal ion.

14. The method of claim 1 wherein the zeolite prepared is ZSM-35 and said reaction mixture has a composition in terms of mole ratios of oxides as follows:

$Al_2O_3/SiO_2 = 0-0.083$
$OH^-/SiO_2 = 0$
$H_2O/SiO_2 = 5-100$
$M/SiO_2 = 0.01-5.0$
$R/SiO_2 = 0.01-1.0$
$H^+(\text{additional})/SiO_2 = 0-1.0$ wherein R is a cation derived from ethylenediamine, propanediamine, butanediamine, or pyrrolidine and M is an alkali metal ion.

* * * * *